United States Patent
Nakamura et al.

(10) Patent No.: US 11,975,318 B2
(45) Date of Patent: May 7, 2024

(54) GRANULE LOADING METHOD

(71) Applicant: Mitsubishi Chemical Corporation, Tokyo (JP)

(72) Inventors: Takuya Nakamura, Tokyo (JP); Daisaku Kaneko, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 387 days.

(21) Appl. No.: 17/444,199

(22) Filed: Aug. 2, 2021

(65) Prior Publication Data
US 2021/0362112 A1 Nov. 25, 2021

Related U.S. Application Data

(63) Continuation of application No. PCT/JP2020/009732, filed on Mar. 6, 2020.

(30) Foreign Application Priority Data

Mar. 29, 2019 (JP) ................................ 2019-066219

(51) Int. Cl.
| | | |
|---|---|---|
| *B01J 8/00* | (2006.01) | |
| *B01J 8/06* | (2006.01) | |
| *B01J 35/50* | (2024.01) | |

(52) U.S. Cl.
CPC ................ *B01J 8/003* (2013.01); *B01J 8/06* (2013.01); *B01J 35/50* (2024.01); *B01J 2208/00752* (2013.01)

(58) Field of Classification Search
CPC .......................... B01J 8/06; B01J 2208/00752
See application file for complete search history.

(56) References Cited

U.S. PATENT DOCUMENTS

| | | | |
|---|---|---|---|
| 3,749,258 A * | 7/1973 | James ...................... | B01J 8/003 53/260 |
| 4,077,530 A | 3/1978 | Fukusen et al. | |
| 5,247,970 A | 9/1993 | Ryntveit et al. | |
| 7,770,613 B2 * | 8/2010 | Brennom ................. | B01J 8/003 141/73 |
| 8,025,472 B2 * | 9/2011 | Fry ........................... | B01J 8/06 414/160 |

(Continued)

FOREIGN PATENT DOCUMENTS

| | | |
|---|---|---|
| CN | 1617843 A | 5/2005 |
| CN | 1826169 A | 8/2006 |

(Continued)

OTHER PUBLICATIONS

Russian Office Action and Search Report dated Jul. 11, 2023 in Russian Patent Application No. 2021128254/04(059678) (with English language translation), 12 pages.

(Continued)

*Primary Examiner* — Timothy P. Kelly
(74) *Attorney, Agent, or Firm* — Oblon, McClelland, Maier & Neustadt, L.L.P.

(57) ABSTRACT

A method may load granules into reaction tubes of a vertical multitube reactor installed vertically by dropping the granules from above each of the reaction tubes whereby a linear member is inserted and suspended in the reaction tube. The reaction tube has an effective length of ≥1000 mm. The linear member includes a small-diameter portion positioned on an upper side and large-diameter portion continuously extending from the small-diameter portion. The small-diameter portion has an outer diameter (Ra) of ≤5.0 mm, and the large-diameter portion has an outer diameter (Rb) of 5.0 to 15.0 mm larger than Ra. A length of the small-diameter portion from reaction tube's upper end is 10.0 mm or more. A distance between an upper surface of a granule loaded layer formed inside the reaction tube and a lower end of the linear member inserted in the reaction tube is ≥100 mm.

20 Claims, 3 Drawing Sheets

(56) References Cited

U.S. PATENT DOCUMENTS

| | | | |
|---|---|---|---|
| 10,279,330 B2* | 5/2019 | McNaughton | B01J 8/003 |
| 2003/0031536 A1 | 2/2003 | Boe et al. | |
| 2004/0250868 A1 | 12/2004 | Yada et al. | |
| 2006/0213575 A1* | 9/2006 | McNaughton | B01J 8/06 |
| | | | 141/286 |
| 2006/0233631 A1 | 10/2006 | Diehl et al. | |
| 2007/0084519 A1 | 4/2007 | Brennom | |
| 2007/0215236 A1* | 9/2007 | Brennom | B01J 8/003 |
| | | | 141/18 |
| 2008/0149215 A1* | 6/2008 | Patureaux | B65G 11/203 |
| | | | 422/232 |
| 2008/0216915 A1 | 9/2008 | Yada et al. | |
| 2008/0234522 A1 | 9/2008 | Yada et al. | |
| 2008/0253943 A1 | 10/2008 | Yoda et al. | |
| 2009/0145727 A1* | 6/2009 | Johns | B01J 8/003 |
| | | | 73/149 |
| 2011/0083769 A1 | 4/2011 | Sanz et al. | |
| 2015/0283528 A1 | 10/2015 | Sanz et al. | |
| 2015/0283529 A1 | 10/2015 | Sanz et al. | |
| 2015/0343404 A1* | 12/2015 | Sanz | B01J 8/002 |
| | | | 141/331 |
| 2018/0141016 A1 | 5/2018 | Cornett et al. | |
| 2020/0353433 A1 | 11/2020 | Cornett et al. | |
| 2022/0274078 A1* | 9/2022 | Brennom | B01J 8/003 |

FOREIGN PATENT DOCUMENTS

| | | |
|---|---|---|
| CN | 1835790 A | 9/2006 |
| CN | 101405214 A | 4/2009 |
| CN | 103097013 A | 5/2013 |
| CN | 109482130 A | 3/2019 |
| EP | 0 548 999 A1 | 6/1993 |
| EP | 1 283 070 A2 | 2/2003 |
| EP | 1 283 070 A3 | 2/2003 |
| EP | 1 466 883 A1 | 10/2004 |
| EP | 1 626 801 B1 | 3/2019 |
| JP | 52-003579 A | 1/1977 |
| JP | 05-031351 A | 2/1993 |
| JP | 2004-195279 A | 7/2004 |
| JP | 2005-169345 A | 6/2005 |
| JP | 2006142299 A | 6/2005 |
| JP | 2006-527070 A | 11/2006 |
| JP | 2011-104507 A | 6/2011 |
| RU | 2396110 C2 | 8/2010 |
| WO | WO 2017/129689 A1 | 8/2017 |

OTHER PUBLICATIONS

Combined Taiwanese Office Action and Search Report dated Apr. 27, 2023 in Patent Application No. 109109104 (with English machine translation and English translation of Category of Cited Documents), 10 pages.

Extended European Search Report dated Apr. 14, 2022 in European Patent Application No. 20783131.4, 15 pages.

International Search Report dated Apr. 28, 2020 in PCT/JP2020/009732 filed on Mar. 6, 2020, 2 pages.

Chinese Office Action and Search Report issued Dec. 19, 2023 in Chinese Patent Application No. 2020800231387.2 (with machine English language translation), 12 pages.

* cited by examiner

GRANULE LOADING METHOD

CROSS-REFERENCE TO RELATED APPLICATIONS

The present application is the bypass continuation of international application PCT/JP2020/009732, filed on Mar. 6, 2020, and claims the benefit of the filing date of Japanese Appl. No. 2019-066219, filed on Mar. 29, 2019.

TECHNICAL FIELD

The present invention relates to a method of loading granules of a catalyst and so on into reaction tubes of a vertical multitube reactor. The present invention relates to a granule loading method capable of smoothly and evenly loading the granules without causing differences in heights of granule loaded layers and loading densities among the individual reaction tubes while preventing damage of the granules and clogging of the reaction tubes with the granules when loaded.

BACKGROUND ART

Hitherto, a vertical multitube reactor has been widely used in a process of producing unsaturated carboxylic acid, such as (meth)acrylic acid, and unsaturated aldehyde.

The vertical multitube reactor includes a tubular barrel (reactor main body), upper and lower tube plates disposed respectively at an upper end and a lower end of the tubular barrel, and a plurality of reaction tubes mounted between the upper and lower tube plates. In the vertical multitube reactor, a raw material fluid is supplied to flow through the reaction tubes, and the raw material fluid in the reaction tubes is heated by a heat transfer medium flowing outside the reaction tubes. With the vertical multitube reactor, efficient reaction can be obtained because the raw material fluid is divided to flow through the plurality of reaction tubes such that application or removal of heat can be evenly performed with the heat transfer medium flowing around the reaction tubes.

Usually, granules of a catalyst (solid catalyst such as a catalyst supported on a carrier) and an inactive substance serving as a dilutant are loaded into the individual reaction tubes of the vertical multitube reactor depending on the purpose of reaction. Those granules need to be evenly loaded into all the reaction tubes in order to form granule loaded layers at an equal height and an equal loading density. If the loading densities and the heights of the granule loaded layers are not equal, there may occur a difference in differential pressure or a bias in flow of the raw material fluid among the reaction tubes when the raw material fluid is supplied to flow through the reaction tubes. Hence even reaction results cannot be obtained in all the reaction tubes.

Also in the case of the granule loaded layer inside one reaction tube, unless the granules are loaded at an equal density in all locations, there occurs a bias in flow of the raw material fluid inside the reaction tube, thus causing a decrease in level of the reaction result.

The decrease in level of the reaction result brings about problems including not only a decrease in reaction yield, a decrease in reaction selectivity, and an increase in byproducts, but also a decrease in catalyst performance and shortening of a catalyst life when the granules are the catalyst.

Hitherto, the loading of the granules into the reaction tube has been performed by putting the granules into the reaction tube installed in a vertical direction from above the reaction tube and causing the granules to drop by gravity. However, this method may physically damage (breaking or powdering) the granules due to impacts caused by the dropping and may bring about uneven loading densities and clogging.

To solve the above-mentioned problem, there are proposed methods of inserting a string-like member, a spiral member, or a chain-like member into the reaction tube and loading the granules with the aid of those members (for example, Patent Literatures (PTL) 1 to 3).

Those methods utilize an effect that a dropping velocity of the granules is reduced because the dropping granules contact the string-like member or the like inserted in the reaction tube (such an effect is called an "assist effect" in this Description). With the reduction in the dropping velocity of the granules, damage of the granules is prevented.

PTL 1: JP5-31351A
PTL 2: JP2004-195279A
PTL 3: JP2005-169345A

The above-described related-art methods have the following problems because due consideration is not paid to an outer diameter of the string-like member and so on.

1) The granules are usually loaded into the reaction tube with the aid of the string-like member through a funnel that is attached to a top of the reaction tube. At that time, the dropping of the granules is impeded by the string-like member. Hence the granules may give rise to clogging at an outlet of the funnel and cannot be smoothly loaded in some cases.

2) Even when the string-like member is used, the granules may be damaged and differences in the loading densities and the heights of the granule loaded layers may be caused among the individual reaction tubes in some cases.

SUMMARY OF INVENTION

An object of the present invention is to provide a granule loading method capable of, when granules are loaded into individual reaction tubes of a vertical multitube reactor, smoothly and evenly loading the granules into the reaction tubes to form granule loaded layers at an equal height while preventing damage of the granules and clogging of the reaction tubes with the granules being loaded.

Solution to Problem

The inventor has found that the above-described problems can be solved by adjusting the outer diameter of the linear member used in loading the granules separately on an upper side and a lower side, and by setting a distance between the granule loaded layer formed in the reaction tube and a lower end of the linear member to be a predetermined value or more.

Summary of the present invention is as follows.

[1] A granule loading method of loading granules into reaction tubes of a vertical multitube reactor installed in a vertical direction by dropping the granules from above each of the reaction tubes without using a funnel, the method loading the granule in a state that a linear member is inserted and suspended in the reaction tube, wherein the reaction tube has an effective length of 1000 mm or more, the linear member inserted in the reaction tube includes a small-diameter portion positioned on an upper side and a large-diameter portion continuously extending from the small-diameter portion, the small-diameter portion has an outer diameter ($R_a$) of 5.0 mm or less, the large-diameter portion has an outer diameter ($R_b$) of 5.0 to 15.0 mm larger than the outer diameter (Ra) of the small-diameter portion, and a length of the small-diameter portion from an upper end of the reaction tube is 10.0 mm or more, and a distance between an upper surface of a granule loaded layer formed inside the reaction tube and a lower end of the linear member inserted in the reaction tube is 100 mm or more.

[2] A granule loading method of loading granules into reaction tubes of a vertical multitube reactor installed in a vertical direction by dropping the granules from above each of the reaction tubes through a funnel, the funnel including a funnel body portion positioned on a side receiving the granules and a leg portion having a cylindrical shape and positioned on a side discharging the granules, the method loading the granules in a state that the leg portion is inserted in the reaction tube and that a linear member is inserted through the leg portion of the funnel and is suspended in the reaction tube, wherein the reaction tube has an effective length of 1000 mm or more, the linear member inserted in the reaction tube includes a small-diameter portion positioned on an upper side and a large-diameter portion continuously extending from the small-diameter portion, the small-diameter portion has an outer diameter (Ra) of 5.0 mm or less, the large-diameter portion has an outer diameter (Rb) of 5.0 to 15.0 mm larger than the outer diameter (Ra) of the small-diameter portion, and a length of the small-diameter portion from a lower end of the leg portion of the funnel is 10.0 mm or more, and a distance between an upper surface of a granule loaded layer formed inside the reaction tube and a lower end of the linear member inserted in the reaction tube is 100 mm or more.

[3] The granule loading method according to [2], wherein an opening diameter of the leg portion of the funnel is not less than 0.6 times an inner diameter of the reaction tube.

[4] The granule loading method according to any one of [1] to [3], wherein the reaction tube has an inner diameter of 22.0 to 35.0 mm.

[5] The granule loading method according to any one of [1] to [4], wherein each of the granules has a size of 3.0 to 15.0 mm.

[6] The granule loading method according to any one of [1] to [5], wherein the vertical multitube reactor is a reactor for producing unsaturated aldehyde.

[7] The granule loading method according to any one of [1] to [5], wherein the vertical multitube reactor is a reactor for producing unsaturated carboxylic acid.

Advantageous Effects of Invention

According to the present invention, when loading the granules into the individual reaction tubes of the vertical multitube reactor, the granules can be evenly and smoothly loaded into the reaction tubes to form the granule loaded layers at an equal height and an equal loading density while damage of the granules is prevented without causing clogging of the reaction tubes with the granules being loaded.

BRIEF DESCRIPTION OF DRAWINGS

FIG. 1 illustrates a reaction tube and a linear member when no funnel is used in a granule loading method according to the present invention; specifically.

DESCRIPTION OF EMBODIMENTS

Embodiments of the present invention will be described in detail below.

[Granule Loading Method in Case of Loading Granules Without Using Funnel]

The granule loading method without using a funnel according to the present invention is a granule loading method of loading granules into reaction tubes of a vertical multitube reactor installed in a vertical direction by dropping the granules from above each of the reaction tubes without using a funnel, the method loading the granule in a state that a linear member is inserted and suspended in the reaction tube, wherein the reaction tube has an effective length of 1000 mm or more, the linear member inserted in the reaction tube includes a small-diameter portion positioned on an upper side and a large-diameter portion continuously extending from the small-diameter portion, the small-diameter portion has an outer diameter (Ra) of 5.0 mm or less, the large-diameter portion has an outer diameter (Rb) of 5.0 to 15.0 mm larger than the outer diameter (Ra) of the small-diameter portion, and a length of the small-diameter portion from an upper end of the reaction tube is 10.0 mm or more, and a distance between an upper surface of a granule loaded layer formed inside the reaction tube and a lower end of the linear member inserted in the reaction tube is 100 mm or more.

The linear member used in the above-described method is described with reference to FIGS. 1a and 1b.

Figure 1A:
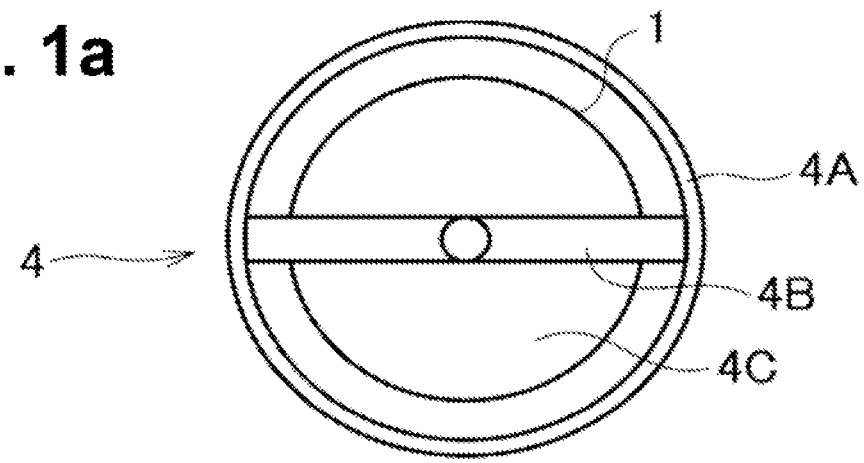
FIG. 1a is a plan view and FIG. 1b is a vertical sectional view.
Figure 1B:
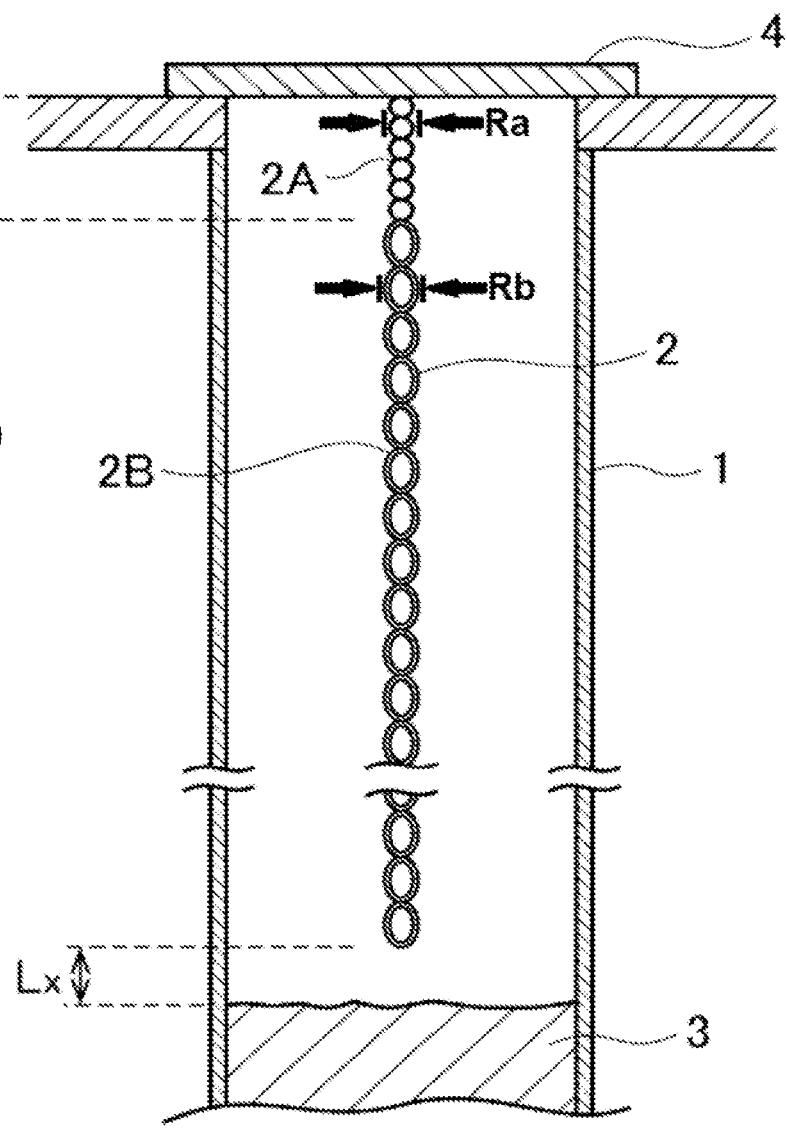

FIGS. 1a and 1b illustrate a state in which the linear member is inserted and suspended in the reaction tube in the method of loading the granules according to the present invention without using the funnel. FIG. 1a is a plan view and FIG. 1b is a vertical sectional view. Reference sign 1 denotes the reaction tube, 2 denotes the linear member, 3 denotes the granule loaded layer 3, and 4 denotes a suspender from which the linear member 2 is suspended.

The linear member 2 has a small-diameter portion 2A on an upper side and a large-diameter portion 2B continuously extending on a lower side from the small-diameter portion 2A in the state in which the linear member 2 is inserted and suspended in the reaction tube 1. The small-diameter portion 2A has an outer diameter (Ra) of 5.0 mm or less, and the large-diameter portion 2B has an outer diameter (Rb) of 5.0 to 15.0 mm larger than the outer diameter (Ra) of the small-diameter portion 2A. A length $L_A$ of the small-diameter portion 2A inside the reaction tube 1, namely the length $L_A$ from an upper end of the reaction tube 1 to a lower end of the small-diameter portion 2A, is 10.0 mm or more. A distance $L_x$ between the upper surface of the granule loaded layer 3 formed inside the reaction tube 1 and the lower end of the linear member 2 inserted in the reaction tube 1 is 100 mm or more.

The outer diameter of the linear member 2 implies a diameter of a portion of the linear member 2, the portion having a maximum diameter in a cross-section perpendicular to a lengthwise direction of the linear member 2.

If the outer diameter (Ra) of the small-diameter portion 2A of the linear member 2 is larger than 5.0 mm, a clogging prevention effect during loading of the granules due to the provision of the small-diameter portion 2A cannot be sufficiently obtained. If the outer diameter (Ra) of the small-diameter portion 2A is too small, the assist effect for the dropping granules due to the provision of the linear member 2 cannot be sufficiently obtained and the strength of the linear member 2 is reduced in some cases. It is preferable that the outer diameter (Ra) of the small-diameter portion 2A be 0.2 mm or more, particularly 1.0 mm or more, and 4.5 mm or less, particularly 3.0 mm or less.

If the length $L_A$ of the small-diameter portion 2A is shorter than 10.0 mm, the clogging prevention effect during loading of the granules due to the provision of the small-diameter portion 2A cannot be sufficiently obtained. If the length $L_A$ of the small-diameter portion 2A is too long, the assist effect for the dropping granules due to the provision of the linear member 2 cannot be sufficiently obtained in some cases. The length $L_A$ of the small-diameter portion 2A is preferably 10.0 to 500 mm and more preferably 10.0 mm to 100 mm.

The outer diameter (Rb) of the large-diameter portion 2B of the linear member 2 is larger than the outer diameter (Ra) of the small-diameter portion 2A and is 5.0 to 15.0 mm. If the outer diameter (Rb) of the large-diameter portion 2B is smaller than 5.0 mm, the assist effect for the dropping granules cannot be sufficiently obtained. If the outer diameter (Rb) of the large-diameter portion 2B is too large, a distance between an inner wall of the reaction tube 1 and the linear member 2 may be too short and the granules cannot be smoothly dropped and loaded. Although depending on an inner diameter of the reaction tube 1 and a size of the granules, it is preferable that the outer diameter (Rb) of the large-diameter portion 2B be 5.0 mm or more, particularly 6.0 mm or more, and 12.0 mm or less, particularly about 10.0 mm or less.

An entire length of the linear member 2 is different depending on an effective length of the reaction tube to which the linear member 2 is applied. As illustrated in FIG. 1b, the entire length of the linear member 2 is set to such a length that, in the state in which the linear member 2 is inserted in the reaction tube 1, the distance $L_x$ between the upper surface of the granule loaded layer 3 formed inside the reaction tube 1 (namely, the upper surface of the granule loaded layer at the end of the loading of the granules 10) and the lower end of the linear member 2 inserted in the reaction tube 1 is 100 mm or more. Stated in another way, the length of the linear member 2 is set such that, in the state in which the linear member 2 is inserted in the reaction tube 1, the lower end of the linear member 2 is positioned 100 mm or more above the upper surface of the granule loaded layer 3 inside the reaction tube 1.

If the distance $L_x$ is shorter than 100 mm, there is a possibility that, for example, when a height of the upper surface of the granule loaded layer 3 exceeds the estimated height, the upper surface of the granule loaded layer 3 may be positioned above the lower end of the linear member 2 and the linear member 2 may impede the loading of the granules.

If the distance $L_x$ is too long, there is a risk that a distance through which the granules are dropped inside the reaction tube 1 without being assisted by the linear member 2 may become too long and the granules may be damaged.

Although depending on the effective length of the reaction tube 1, the length of the linear member 2 is preferably designed such that, in the state in which the linear member 2 is inserted in the reaction tube 1, the granule loaded layer 3 is formed with the distance $L_x$ being 100 to 1500 mm, particularly 100 to 1200 mm, and with the layer height being 300 to 2500 mm, particularly 300 to 2000 mm.

Although depending on the effective length of the reaction tube 1, it is preferable that the distance $L_x$ be 2% or more, particularly 3% or more, and 50% or less, particularly 40% or less, of the effective length of the reaction tube 1.

Between the small-diameter portion 2A and the large-diameter portion 2B, the linear member 2 may have a medium-diameter portion with an intermediate diameter therebetween. The diameters of the small-diameter portion 2A and the large-diameter portion 2B may be changed in a stepwise manner or may be continuously changed. The diameter may be gradually increased from the small-diameter portion 2A toward the large-diameter portion 2B.

There are no specific limitations on materials and forms of the linear member 2 insofar as the materials and the forms can assist the drop of the granules in a way of reducing the dropping velocity without impeding the drop of the granules.

Examples of the materials of the linear member 2 may be stainless and plastics.

The linear member 2 may be in the form of, for example, a thread (string), a chain, and a spiral. The linear member 2 is preferably a chain. In the linear member 2, more preferably, the small-diameter portion 2A is a ball chain constituted by connecting balls with an outer diameter equal to the above-mentioned outer diameter (Ra) of the small-diameter portion 2A, and the large-diameter portion 2B is a ring chain constituted by connecting rings with an outer diameter equal to the above-mentioned outer diameter (Rb) of the large-diameter portion 2B.

Two or more linear members may be inserted in the reaction tube. However, if too many linear members are inserted in the reaction tube, the linear members may impede the dropping of the granules contrary to the intent. Although depending on the size of the reaction tube, it is generally preferable that the single linear member 2 is inserted and suspended on a center axis of the reaction tube 1.

The linear member 2 may be inserted and suspended in the reaction tube 1, as illustrated in FIGS. 1a and 1b, by mounting a suspender 4 to an upper open end of the reaction tube 1, the suspender 4 including a ring 4A larger than the outer diameter of the reaction tube 1 and a rod 4B which is disposed to extend across the ring 4A in a radial direction and to which the linear member 2 is attached, and by attaching the linear member 2 to the suspender 4 to be inserted and suspended in the reaction tube 1.

The granules enter the reaction tube 1 through an opening 4C of the suspender 4 and are dropped to be loaded in the reaction tube 1 with the aid of the linear member 2.

[Granule Loading Method in Case of Loading Granules by Using Funnel]

The granule loading method using a funnel according to the present invention is a granule loading method of loading granules into reaction tubes of a vertical multitube reactor installed in a vertical direction by dropping the granules from above each of the reaction tubes through a funnel, the funnel including a funnel body portion positioned on a side receiving the granules and a leg portion having a cylindrical shape and positioned on a side discharging the granules, the method loading the granules in a state that the leg portion is inserted in the reaction tube and that a linear member is inserted through the leg portion of the funnel and is suspended in the reaction tube, wherein the reaction tube has an effective length of 1000 mm or more, the linear member inserted in the reaction tube includes a small-diameter portion positioned on an upper side and a large-diameter portion continuously extending from the small-diameter portion, the small-diameter portion has an outer diameter (Ra) of 5.0 mm or less, the large-diameter portion has an outer diameter (Rb) of 5.0 to 15.0 mm larger than the outer diameter (Ra) of the small-diameter portion, and a length of the small-diameter portion from a lower end of the leg portion of the funnel is 10.0 mm or more, and a distance between an upper surface of a granule loaded layer formed inside the reaction tube and a lower end of the linear member inserted in the reaction tube is 100 mm or more.

The linear member and the funnel used in the above-described method are described with reference to FIG. 2.

Figure 2:
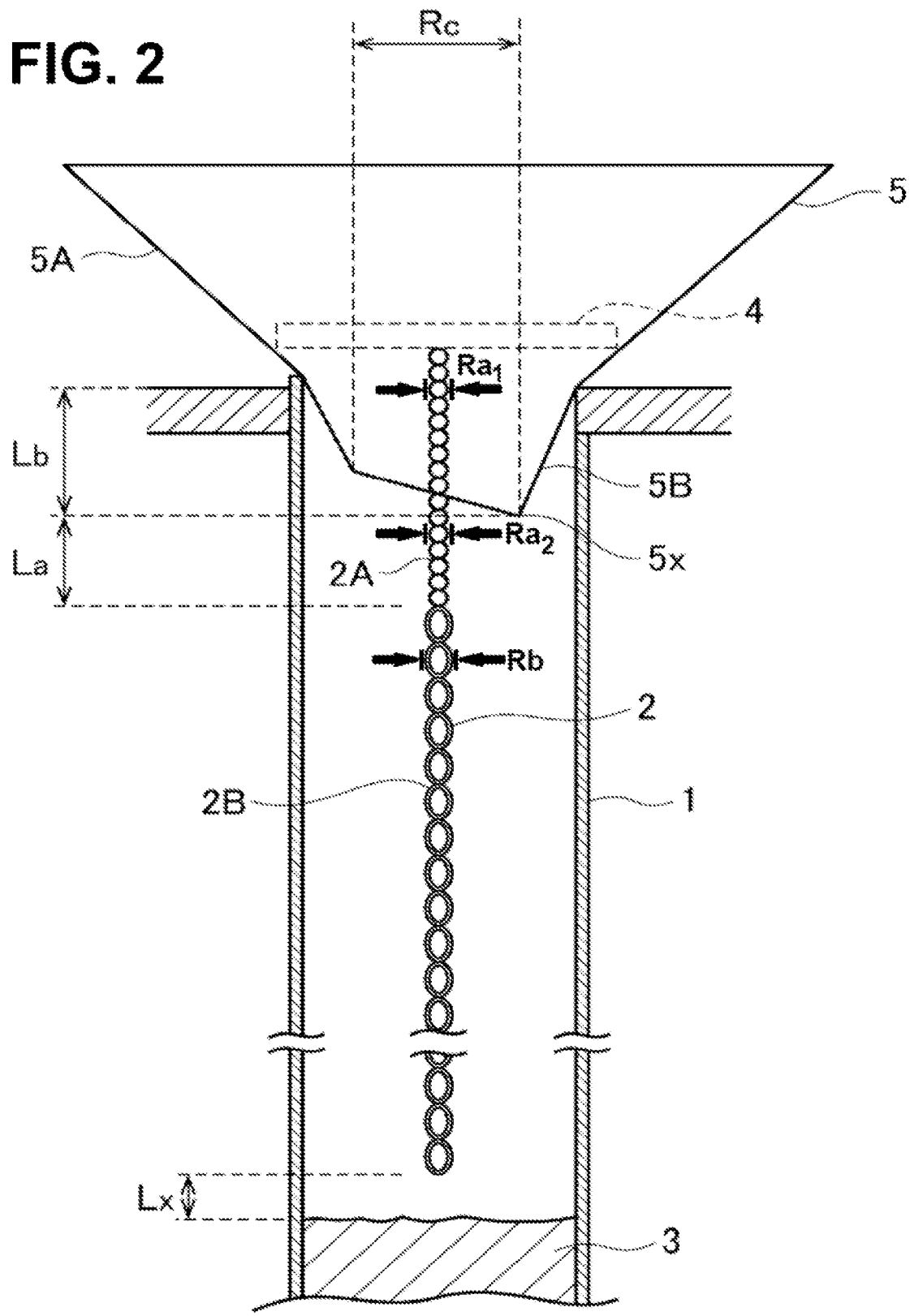
FIG. 2 is a vertical sectional view illustrating a reaction tube and a linear member when a funnel is used in a granule loading method according to the present invention.

FIG. 2 is a vertical sectional view illustrating a state in which the linear member is inserted and suspended in the reaction tube through the funnel in the method of loading the granules according to the present invention with use of the funnel. In FIG. 2, members with similar functions to those illustrated in FIG. 1 are denoted by the same reference signs. Reference sign 5 denotes the funnel.

The funnel 5 includes a large-diameter funnel body portion 5A positioned on a side receiving the granules, and a leg portion 5B positioned on a side discharging the granules. The funnel body portion 5A has a substantially inverted cone shape with a diameter gradually reducing toward the leg portion 5B. The leg portion 5B has a cylindrical shape with a diameter further gradually reducing. Although the leg portion 5B of the funnel 5 illustrated in FIG. 2 has the diameter gradually reducing downward, the leg portion 5B may have a cylindrical shape with a uniform diameter. A lower discharge opening of the leg portion 5B has an obliquely cut-out shape, but it may be formed in a horizontal plane.

An outer diameter (Rc) of the leg portion 5B of the funnel 5 implies a diameter of a portion of the leg portion 5B, the portion having a minimum diameter. A lower end of the leg portion 5B is a discharge tip end of the leg portion 5B and is denoted by 5x in FIG. 2.

The linear member 2 has a small-diameter portion 2A positioned on an upper side and a large-diameter portion 2B positioned on a lower side and continuously extending from the small-diameter portion 2A in the state in which the linear member 2 is inserted and suspended in the reaction tube 1 through the funnel 5. The small-diameter portion 2A has an outer diameter (Ra) of 5.0 mm or less, and the large-diameter portion 2B has an outer diameter (Rb) of 5.0 to 15.0 mm larger than the outer diameter (Ra) of the small-diameter portion 2A. A length $L_a$ from the lower end 5x of the leg portion 5B of the funnel 5 inside the reaction tube 1 to the lower end of the small-diameter portion 2A is 10.0 mm or more. A distance $L_x$ between the upper surface of the granule loaded layer 3 formed inside the reaction tube 1 and the lower end of the linear member 2 inserted in the reaction tube 1 is 100 mm or more.

As described above, the outer diameter of the linear member 2 implies a diameter of a portion of the linear member 2, the portion having a maximum diameter in a cross-section perpendicular to the lengthwise direction of the linear member 2.

If the outer diameter (Ra) of the small-diameter portion 2A of the linear member 2 is larger than 5.0 mm, a clogging prevention effect during loading of the granules due to the provision of the small-diameter portion 2A cannot be sufficiently obtained. If the outer diameter (Ra) of the small-diameter portion 2A is too small, the assist effect for the dropping granules due to the provision of the linear member 2 cannot be sufficiently obtained and the strength of the linear member 2 is reduced in some cases. It is preferable that the outer diameter (Ra) of the small-diameter portion 2A be 0.2 mm or more, particularly 1.0 mm or more, and 4.5 mm or less, particularly 3.0 mm or less.

If the length $L_a$ of the small-diameter portion 2A from the lower end 5x of the leg portion 5B of the funnel 5 is shorter than 10.0 mm, the clogging prevention effect during loading of the granules due to the provision of the small-diameter portion 2A cannot be sufficiently obtained. If the length $L_a$ of the small-diameter portion 2A is too long, the assist effect for the dropping granules due to the provision of the linear member 2 cannot be sufficiently obtained in some cases. The length $L_a$ of the small-diameter portion 2A is preferably 10.0 to 500 mm and more preferably 10.0 mm to 100 mm.

An outer diameter (Ra) of the large-diameter portion 2B of the linear member 2, a distance $L_x$ between the lower end of the linear member 2 and the upper surface of the granule loaded layer 3, a length of the linear member 2 in the state inserted in the reaction tube, a height of the granule loaded layer 3 to be formed, and materials and forms of the linear member 2 are as per described above in connection with the embodiment illustrated in FIGS. 1a and 1b.

In the embodiment illustrated in FIG. 2, the small-diameter portion 2A of the linear member 2 may be constituted by a first small-diameter portion positioned inside the funnel 5, and a second small-diameter portion extending downward from the leg portion 5B of the funnel 5, and an outer diameter ($Ra_1$) of the first small-diameter portion may be set equal to or smaller than an outer diameter ($Ra_2$) of the second small-diameter portion.

An upper region of the small-diameter portion 2A of the linear member 2 is a region passing through the funnel 5. If a spacing between an inner wall of the leg portion 5B of the funnel 5 and the small-diameter portion 2A is too small, the loading of the granules may be impeded in some cases. To secure the above-mentioned spacing, the outer diameter ($Ra_1$) of the first small-diameter portion is preferably set as small as possible.

In such a case, the outer diameter ($Ra_2$) of the second small-diameter portion is equal to the above-mentioned outer diameter (Ra) of the small-diameter portion 2A. The outer diameter ($Ra_1$) of the first small-diameter portion is preferably set to be 5.0 mm or less, particularly 3.0 mm or less, and 1.0 mm or more.

In this embodiment using the funnel 5, there are no specific limitations on the funnel 5. An opening diameter (Rc) of the leg portion 5B is preferably not less than 0.6 times, more preferably 0.65 times or more, furthermore preferably not less than 0.7 times, even more preferably not less than 0.75 times, still even more preferably not less than 0.8 times, and most preferably not less than 0.85 times an inner diameter of the reaction tube 1. By setting the outer diameter (Rc) of the leg portion 5B to be not less than the above-mentioned lower limit value, smooth loading can be ensured while suppressing the clogging even when a loading rate is increased. There are no specific limitations on an upper limit of the opening diameter (Rc) of the leg portion 5B, and the outer diameter of the leg portion 5B may be equal to the inner diameter of the reaction tube 1.

A length ($L_b$ in FIG. 2) through which the leg portion 5B of the funnel is inserted into the reaction tube 1 is usually about 20 to 70 mm.

In the embodiment of FIG. 2, after being put into the body portion 5A of the funnel 5, the granules pass through the opening 4C of the suspender 4 disposed within the body portion 5A and enter the reaction tube 1 through the leg portion 5B of the funnel 5 to be dropped and loaded into the reaction tube 1 with the aid of the linear member 2.

[Reaction Tube]

Regardless of whether the funnel is used or not, the reaction tube 1 to which the present invention is applied is a reaction tube disposed in a vertical multitube reactor and has an effective length of 1000 mm or more. The effective length implies a length of a void tower region in the reaction tube and is usually almost equal to a distance between an upper pipe plate and a lower pipe plate of the vertical multitube reactor.

If the effective length of the reaction tube 1 is less than 1000 mm, damage caused by the dropping of the granules during the loading is less problematic even when the present invention is not applied. From that point of view, the effect length of the reaction tube 1 is preferably 1000 mm or more and more preferably 1100 mm or more. On the other hand, the effective length of the reaction tube 1 is usually 10000 mm or less from the viewpoint of limitations on the size of the vertical multitube reactor.

The inner diameter of the reaction tube 1 is preferably 22.0 mm or more and more preferably 24.0 mm or more from the viewpoint of dropping and loading the granules of a later-described size by using the linear member 2 with the above-described outer diameter. If the inner diameter of the reaction tube 1 is too large, the assist effect for the dropping granules cannot be sufficiently obtained even with the use of the linear member 2. Furthermore, if the inner diameter of the reaction tube 1 is too large, an effect of heating the reaction tube or removing heat from the reaction tube by using the vertical multitube reactor is reduced and an effect resulting from disposing the plurality of reaction tubes with a relatively small diameter is reduced. For that reason, the inner diameter of the reaction tube 1 is preferably 35.0 mm or less and more preferably 30.0 mm or less.

[Granule]

Regardless of whether the funnel is used or not, there are no specific limitations on the type of the granule to be loaded into the reaction tube 1 in the present invention. The granule may be a catalyst for use in reaction, or an inactive substance serving as a dilutant.

There are no specific limitations on the shape of the granule, and the granule may have any of a spherical shape, a columnar shape, a cylindrical shape, a ring-like shape, a dice-like shape, a flake-like shape, a mesh-like shape, and other indefinite shapes.

There are no specific limitations on the size of the granule. The granule size is preferably 3.0 to 15.0 mm and more preferably 5.0 to 15.0 mm from the viewpoint of smoothly loading the granules without causing damage and clogging by using the linear member 2 and the reaction tube 1 of the above-described sizes. If the granule size is less than the above-mentioned lower limit value, a gap between the granules inside the reaction tube may be so small that a differential pressure tends to rise, for example, when the granule is a catalyst and the reaction tube is a reaction tube for gas-phase reaction in which raw material gas is supplied from one end and reaction product gas is discharged from the other end. If the granule size exceeds the above-mentioned upper limit value, a contact area of the granule with the raw material gas per unit volume of the granule may be reduced and the gas-phase reaction may tend to be insufficient.

The granule size implies a size of a portion of the granule in which, when sandwiching the granule between two parallel plates, a spacing between those two plates is maximized. For example, when the granule is in the form of a sphere, the granule size is a diameter of the sphere.

Figure 3:
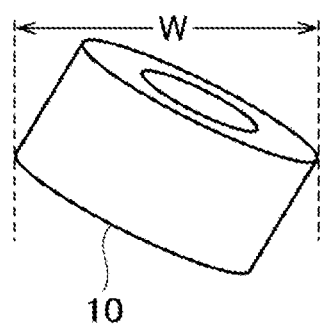
FIG. 3 is a perspective view illustrating a granule size.

When the granule 10 has a ring-like shape, a cylindrical shape, or a columnar shape, the size of the granule 10 is given by W denoted in FIG. 3.

Here, $$W^2 = (\text{outer diameter of granule 10})^2 + (\text{height of granule 10})^2$$

For example, in the case of a Raschig ring-shaped granule with an outer diameter of 10 mm, an inner diameter of 6 mm, and a height of 10 mm, which is used in Examples described later, $$W^2 = 10^2 + 10^2$$

$$W = \sqrt{(2)} \times 10 = 14.1 \text{ mm}.$$

The granules to be loaded into the reaction tube may be only one type or may be a mixture of two or more types of granules that are different in constituent material, shape, and/or size.

A granule loaded layer constituted by two or more layers of different types of granules in a height direction may be formed by loading granules I in an initial stage of the loading and then loading granules II different from the granules I.

There are no specific limitations on a granule loading rate. The granule loading rate is different depending on the size of the granules, the size of the reaction tube, the form of the linear member used, the mechanical strength of the granules, and so on. In the case of the granules with the size of 3.0 to 15.0 mm, for example, the clogging with the granules can be easily suppressed by setting the granule loading rate such a value that a loaded volume per second is 10.0 to 50 cc.

[Production of Unsaturated Aldehyde and Unsaturated Carboxylic Acid]

There are no specific limitations on application fields of the granule loading method according to the present invention. The advantageous effects of the granule loading method according to the present invention are effectively developed especially when granules of a catalyst and so on are loaded into the reaction tubes of the vertical multitube reactor that is used to produce unsaturated aldehyde and unsaturated carboxylic acid.

A method of loading the catalyst into the vertical multitube reactor for producing unsaturated carboxylic acid with unsaturated aldehyde being the intermediate will be described below.

As catalysts for use in producing unsaturated carboxylic acid such as (meth)acrylic acid, there are a catalyst used for the 1st stage reaction from olefin (propylene or isobutylene) to unsaturated aldehyde or unsaturated carboxylic acid, a catalyst used for the second stage reaction from unsaturated aldehyde to unsaturated carboxylic acid, and a catalyst used for reaction from alkane to unsaturated carboxylic acid.

An example of the catalyst used in the first stage reaction is expressed by the following general formula (I).

$$Mo_a W_b Bi_c Fe_d A_e B_f C_g D_h E_i O_x \tag{I}$$

In the general formula (I), Mo is molybdenum, W is tungsten, Bi is bismuth, and Fe is iron. A is at least one type of element selected from nickel and cobalt. B is at least one type of element selected from sodium, kalium, rubidium, cesium, and thallium. C is at least one type of element selected from alkaline earth metals. D is at least one type of element selected from phosphorus, tellurium, antimony, tin, cerium, lead, niobium, manganese, arsenic, boron, and zinc. E is at least one type of element selected from silicon, aluminum, titanium, and zirconium. O is oxygen.

Furthermore, a, b, c, d, e, f, g, h, i and x denote atomic ratios of Mo, W, Bi, Fe, A, B, C, D, E and O, respectively. In the case of a=12, 0≤b≤10, 0<c≤10 (preferably 0.1≤c≤10), 0<d≤10 (preferably 0.1≤d≤10), 2≤e≤15, 0≤f≤10, 0≤g≤10, $0 \leq h \leq 4$, and $0 \leq i \leq 30$ are satisfied. Moreover, x denotes a value that is determined depending on oxidation states of the individual elements.

An example of the catalyst used in the second stage reaction is expressed by the following general formula (II).

$$Mo_aV_bX_cCu_dY_eSb_fZ_gSi_hC_iO_j \quad (II)$$

In the general formula (II), Mo is molybdenum, and V is vanadium. X is at least one type of element selected from niobium and tungsten. Cu is copper. Y is at least one type of element selected from magnesium, calcium, strontium, barium, and zinc. Z is at least one type of element selected from iron, cobalt, nickel, titanium, and bismuth. Si is silicon, C is carbon, and O is oxygen.

Furthermore, a, b, c, d, e, f, g, h and j denote atomic ratios of Mo, V, X, Cu, Y, Sb, Z, Si, C and O, respectively. In the case of a=12, $0<b\leq12$, $0\leq c\leq12$, $0<d\leq12$, $0\leq e\leq8$, $0\leq f\leq500$, $0\leq g\leq500$, $0\leq h\leq500$, and $0\leq i\leq500$ are satisfied. Moreover, j denotes a value that is determined depending on oxidation states of the individual elements.

The above-mentioned catalysts can be each produced by mixing aqueous solutions of water-soluble salts of the predetermined metal components under the presence of a carrier, for example, silica or alumina, as required, drying the resulting mixture, molding the dried mixture into a desired shape, and firing it.

The above-mentioned catalysts may be each a molded catalyst that is formed by an extrusion method or a tableting method, or a supported catalyst in which a composite oxide made of catalyst components is supported on an inactive carrier such as silicon carbide, alumina, zirconium oxide, or titanium oxide.

There are no specific limitations on the shape of the catalyst. The catalyst may have any of a spherical shape, a columnar shape, a cylindrical shape, a ring-like shape, a star-like shape, and other indefinite shapes. Particularly, using the ring-shaped catalyst is effective in preventing accumulation of heat in a hot area.

The above-mentioned catalyst substance can also be used in combination with an inactive substance. After combining the inactive substance with the catalyst substance, the resulting mixture may be molded into particles in a similar shape to that of the catalyst by a similar method to that described above. Instead, after molding the inactive substance into inactive particles in an appropriate shape, those particles may be combined with particles that are molded in a similar manner by using the catalyst substance.

There are no specific limitations on the inactive substance insofar as it is stable and does not affect the reaction in the reaction tube, and the inactive substance is determined as appropriate depending on the intended use. Various types of inactive materials known in the art can be optionally used as the inactive substance. Examples of the inactive substance are refractories such as alumina, zirconium oxide, titanium oxide, alundum, mullite, carborundum, stainless steel, silicon carbide, steatite, pottery, porcelain, iron, and various ceramics.

There are no specific limitations on the shape of the inactive particle made of the inactive substance. The inactive particles may have, for example, a spherical shape, a columnar shape, a cylindrical shape, a metal mesh-like shape, or a plate-like shape. Packings made of the inactive substance are commercially available in various shapes. Examples of the packings that can be easily available in substantially the same shape are a Raschig ring, an interlock saddle, a Berl saddle, a ceramic ball, a McMahon packing, and a Dixon packing.

An amount of the inactive substance used is determined as appropriate depending on the object catalytic activity. For example, it is preferable to employ a method of dividing a layer of the catalyst loaded in the reaction tube and increasing the amount of the inactive substance used in an region near an inlet for the raw material gas to reduce the catalytic activity and to suppress a temperature of the catalyst layer from rising too high in that region due to excessive reaction, and/or reducing the amount of the inactive substance used in an region near an outlet for reaction gas to increase the catalytic activity, to promote the reaction, and to suppress the raw material gas from remaining too much.

The following description is made on an assumption of a fixed-bed catalyst layer in which the raw material gas is introduced from above. A fluid-bed catalyst layer in which the raw material gas is introduced from below may also be used.

A heat transfer medium is heated by appropriate means, for example, a heating apparatus such as a boiler or an electric heater, to a temperature at which the introduced raw material gas starts the reaction. When the reaction is gas-phase contact oxidation reaction, the heat transfer medium functions as a coolant to absorb heat generated with the oxidation reaction after the start of the reaction. In that case, the heat transfer medium is guided to appropriate means, such as a heat exchanger, and is cooled as required.

As typical industrialized methods for the gas-phase contact oxidation reaction to produce unsaturated aldehyde and (meth)acrylic acid, there are a one-pass method, an unreacted alkane recycle method, and a combustion waste gas recycle method.

According to the one-pass method, in the first stage reaction, alkane such as propylene (or isobutylene), air, and water vapor are mixed and supplied through a reaction raw-material gas inlet of each reaction tube of a vertical multitube reactor for the first stage reaction, thereby converting the alkane mainly to unsaturated aldehyde, such as meth(acrolein), and unsaturated carboxylic acid, such as (meth)acrylic acid. Outlet gas is supplied to each reaction tube of a vertical multitube reactor for the second stage reaction without being separated from products, thereby oxidizing the unsaturated aldehyde, such as the meth(acrolein), to the unsaturated carboxylic acid, such as the (meth)acrylic acid. At that time, it is also general to supply air and water vapor, which are necessary for development of the second stage reaction, to carry out the second stage reaction in addition to the outlet gas from the first stage reaction.

According to the unreacted alkane recycle method, reaction product gas containing the unsaturated carboxylic acid, such as the (meth)acrylic acid, and obtained at the outlet of the second stage reaction is introduced to an apparatus for capturing the unsaturated carboxylic acid, and the unsaturated carboxylic acid is captured in an aqueous solution. Part of waste gas containing the unreacted alkane is supplied from the capturing apparatus to the reaction raw-material gas inlet for the first stage reaction, whereby part of the unreacted alkane is recycled.

According to the combustion waste gas recycle method, the reaction product gas containing the unsaturated carboxylic acid and obtained at the outlet of the reactor for the second stage reaction is introduced to the apparatus for capturing the unsaturated carboxylic acid, and the unsaturated carboxylic acid is captured in an aqueous solution. All waste gas from the capturing apparatus is oxidized by combustion in a contact manner, whereby the unreacted alkane and so on contained in the waste gas is converted to mainly carbon dioxide and water. Part of waste gas obtained by the combustion is supplied to the raw-material gas inlet for the first stage reaction.

In the above-described reaction performed using the vertical multitube reactor, a gas mixture of, for example, 4 to 15% by volume of propylene, 4 to 30% by volume of oxygen, 0 to 60% by volume of water vapor, and 20 to 80% by volume of inert gas, such as nitrogen or carbon dioxide, is introduced to the catalyst layer at 250 to 450° C., under pressure of 50 to 200 kPa, and at a space velocity (SV) of 300 to 5000 $hr^{-1}$.

EXAMPLES

The present invention will be described in more detail below with reference to EXAMPLES. The present invention is not limited to the following examples insofar as not departing from the gist of the present invention.

<Measurement of Broken Rate>

Granules loaded into a reaction tube was taken out and the weight of the granules was measured. Of the taken-out granules, broken ones were visually selected and collected. The weight of the collected broken granules was measured, and a broken rate was calculated using the following formula.

Broken rate (% by weight)=(weight of broken granules/weight of taken-out granules)×100

Example 1

Granules were loaded in accordance with the embodiment, illustrated in FIG. 2, using the funnel.

Two reaction tubes made of vinyl chloride and having an inner diameter of 30 mm and a tube length of 4000 mm (effective length of 4000 mm) were installed in the vertical direction. An aluminum-made funnel (of which leg portion had an opening diameter of 22.5 mm) was attached to a top of each of the two reaction tubes. A suspender was disposed inside a conical body portion of the aluminum-made funnel. One end of a linear member was fixed to the suspender such that the linear member extended downward in the vertical direction within the leg portion of the aluminum-made funnel and the reaction tube along a center axis of the reaction tube. The linear member was a linear member (length of 2630 mm) including a ball chain having an outer diameter of 3 mm and positioned on an upper side in the vertical direction, and a ring chain (outer diameter of 7 mm) constituted by elliptic ring-like members with a horizontal width of 7 mm×a vertical length of 12 mm and positioned on a lower side in the vertical direction, the ball chain and the ring chain being connected in series. Of the linear member extending downward in the vertical direction from the suspender, the ball chain with the outer diameter of 3 mm extended downward over a range of 20 mm from a lower end of the leg portion of the funnel, and the ring chain (outer diameter of 7 mm) constituted by the elliptic ring-like members with the horizontal width of 7 mm×the vertical length of 12 mm extended below the ball chain. The outer diameter (Ra) of a small-diameter portion of the linear member was 3 mm, the length $L_a$ of the small-diameter portion from the lower end of the leg portion of the funnel was 20 mm, the outer diameter (Rb) of a large-diameter portion of the linear member was 7 mm, and the length of the large-diameter portion was 2380 mm. The length $L_b$ through which the leg portion of the funnel was inserted in the reaction tube was 50 mm.

Then, 234 g of Raschig ring-shaped granules (size of 14.1 mm) made of silica-alumina and having an outer diameter of 10 mm, an inner diameter of 6 mm, and a height of 10 mm were dropped and loaded into each of the two reaction tubes from above the reaction tube through the funnel at a rate of the loaded volume of 30 cc per second. At the end of the dropping and the loading, the distance between a lower end of the linear member and an upper surface of a granule loaded layer was 1110 mm. In other words, the length $L_x$ in FIG. 2 was 1110 mm.

As a result of dropping and loading the granules, clogging with the granules did not occur in both the two reaction tubes. The broken rates of the granules loaded in the two reaction tubes were 0.9% by weight and 0.9% by weight, namely the same. The heights of the granule loaded layers in the two reaction tubes were 440 mm and 440 mm, namely the same. Because of the broken rates and the heights of the granule loaded layers being the same, it can be said that the loading densities in the two reaction tubes are also the same.

Example 2

Granules were loaded in accordance with the embodiment, illustrated in FIG. 1, not using the funnel.

Two reaction tubes made of vinyl chloride and having an inner diameter of 25 mm and a tube length of 2000 mm (effective length of 2000 mm) were installed in the vertical direction. A suspender was disposed at a top of each of the two reaction tubes. One end of a linear member was fixed to the suspender such that the linear member extended downward in the vertical direction within the reaction tube along a center axis of the reaction tube. The linear member was a linear member (length of 1290 mm) including a ball chain having an outer diameter of 3 mm and positioned on an upper side in the vertical direction, and a ring chain (outer diameter of 7 mm) constituted by elliptic ring-like members with a horizontal width of 7 mm×a vertical length of 12 mm and positioned on a lower side in the vertical direction, the ball chain and the ring chain being connected in series. Of the linear member, the ball chain with the outer diameter of 3 mm extended downward in the vertical direction over a range of 50 mm from the suspender, and the ring chain (outer diameter of 7 mm) constituted by the elliptic ring-like members with the horizontal width of 7 mm×the vertical length of 12 mm extended below the ball chain. The outer diameter (Ra) of a small-diameter portion of the linear member was 3 mm, the length $L_A$ of the small-diameter portion was 50 mm, the outer diameter (Rb) of a large-diameter portion of the linear member was 7 mm, and the length of the large-diameter portion was 1240 mm.

Then, 273 g of granules (size of 5.53 mm) of a catalyst used to produce unsaturated aldehyde, the granules having a spherical shape with an average granule diameter of 5.53 mm, were dropped and loaded into each of the two reaction tubes from above the reaction tube at a rate of the loaded volume of 30 cc per second. At the end of the dropping and the loading, the distance between a lower end of the linear member and an upper surface of a granule loaded layer was 200 mm. In other words, the length $L_x$ in FIG. 1 was 200 mm.

An atomic ratio among catalytic active elements of the catalyst used to produce the unsaturated aldehyde was as follows:

$$Mo_{12}Bi_{2.9}Fe_{0.8}Co_{3.4}Ni_{3.4}$$

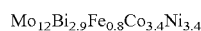

As a result of dropping and loading the granules, clogging with the granules did not occur in both the two reaction tubes. The heights of the granule loaded layers in the two reaction tubes were 510 mm and 510 mm, namely the same. Because of the heights of the granule loaded layers being the same, it can be said that the loading densities in the two reaction tubes are also the same.

Example 3

Granules were loaded in accordance with the embodiment, illustrated in FIG. 2, using the funnel.

Two reaction tubes made of vinyl chloride and having an inner diameter of 25 mm and a tube length of 2000 mm (effective length of 2000 mm) were installed in the vertical direction. An aluminum-made funnel (of which leg portion had an opening diameter of 22.5 mm) was attached to a top of each of the two reaction tubes. A suspender was disposed inside a conical body portion of the aluminum-made funnel. One end of a linear member was fixed to the suspender such that the linear member extended downward in the vertical direction within the leg portion of the aluminum-made funnel and the reaction tube along a center axis of the reaction tube. The linear member was a linear member (length of 1470 mm) including a ball chain having an outer diameter of 3 mm and positioned on an upper side in the vertical direction, and a ring chain (outer diameter of 7 mm) constituted by elliptic ring-like members with a horizontal width of 7 mm×a vertical length of 12 mm and positioned on a lower side in the vertical direction, the ball chain and the ring chain being connected in series. Of the linear member extending downward in the vertical direction from the suspender, the ball chain with the outer diameter of 3 mm extended downward over a range of 20 mm from a lower end of the leg portion of the funnel, and the ring chain (outer diameter of 7 mm) constituted by the elliptic ring-like members with the horizontal width of 7 mm×the vertical length of 12 mm extended below the ball chain. The outer diameter (Ra) of a small-diameter portion of the linear member was 3 mm, the length $L_a$ of the small-diameter portion from the lower end of the leg portion of the funnel was 20 mm, the outer diameter (Rb) of a large-diameter portion of the linear member was 7 mm, and the length of the large-diameter portion was 1220 mm. The length $L_b$ through which the leg portion of the funnel was inserted in the reaction tube was 50 mm.

Then, 273 g of granules (size of 5.53 mm) of a catalyst used to produce unsaturated aldehyde, the granules being similar to those used in EXAMPLE 2 and having a spherical shape with an average granule diameter of 5.53 mm, were dropped and loaded into each of the two reaction tubes from above the reaction tube through the funnel at a rate of the loaded volume of 30 cc per second. At the end of the dropping and the loading, the distance between a lower end of the linear member and an upper surface of a granule loaded layer was 200 mm. In other words, the length $L_x$ in FIG. 2 was 200 mm.

As a result of dropping and loading the granules, clogging with the granules did not occur in both the two reaction tubes. The heights of the granule loaded layers in the two reaction tubes were 510 mm and 510 mm, namely the same. Because of the heights of the granule loaded layers being the same, it can be said that the loading densities in the two reaction tubes are also the same.

Example 4

Granules were dropped and loaded at a rate of the loaded volume of 30 cc per second in a similar manner to that in EXAMPLE 2 except for using, as the granules to be loaded, 287 g of granules (size of 5.16 mm) of a catalyst used to produce unsaturated carboxylic acid, the granules having a spherical shape with an average granule diameter of 5.16 mm, instead of the granules of the catalyst having been used to produce the unsaturated aldehyde, the latter granules having the spherical shape with the average granule diameter of 5.53 mm. At the end of the dropping and the loading, the distance between the lower end of the linear member and an upper surface of a granule loaded layer was 190 mm. In other words, the length $L_x$ in FIG. 1 was 190 mm.

An atomic ratio among catalytic active elements of the catalyst used to produce the unsaturated carboxylic acid was as follows:

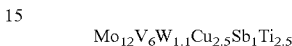

$$Mo_{12}V_6W_{1.1}Cu_{2.5}Sb_1Ti_{2.5}$$

As a result of dropping and loading the granules, clogging with the granules did not occur in both the two reaction tubes. The heights of the granule loaded layers in the two reaction tubes were 520 mm and 520 mm, namely the same. Because of the heights of the granule loaded layers being the same, it can be said that the loading densities in the two reaction tubes are also the same.

Example 5

Granules were dropped and loaded at a rate of the loaded volume of 30 cc per second in a similar manner to that in EXAMPLE 3 except for using, as the granules to be loaded, 287 g of granules (size of 5.16 mm) of a catalyst used to produce unsaturated carboxylic acid, the granules being similar to those used in EXAMPLE 4 and having a spherical shape with an average granule diameter of 5.16 mm, instead of the granules of the catalyst having been used to produce the unsaturated aldehyde, the latter granules having the spherical shape with the average granule diameter of 5.53 mm. At the end of the dropping and the loading, the distance between the lower end of the linear member and an upper surface of a granule loaded layer was 190 mm. In other words, the length $L_x$ in FIG. 1 was 190 mm.

As a result of dropping and loading the granules, clogging with the granules did not occur in both the two reaction tubes. The heights of the granule loaded layers in the two reaction tubes were 520 mm and 520 mm, namely the same. Because of the heights of the granule loaded layers being the same, it can be said that the loading densities in the two reaction tubes are also the same.

Example 6

Granules were loaded in accordance with the embodiment, illustrated in FIG. 1, not using the funnel.

Two reaction tubes made of vinyl chloride and having an inner diameter of 25 mm and a tube length of 2000 mm (effective length of 2000 mm) were installed in the vertical direction. A suspender was disposed at a top of each of the two reaction tubes. One end of a linear member was fixed to the suspender such that the linear member extended downward in the vertical direction within the reaction tube along a center axis of the reaction tube. The linear member was a linear member (length of 1400 mm) including a ball chain having an outer diameter of 3 mm and positioned on an upper side in the vertical direction, and a ring chain (outer diameter of 7 mm) constituted by elliptic ring-like members with a horizontal width of 7 mm×a vertical length of 12 mm and positioned on a lower side in the vertical direction, the ball chain and the ring chain being connected in series. Of the linear member, the ball chain with the outer diameter of 3 mm extended downward in the vertical direction over a range of 50 mm from the suspender, and the ring chain (outer diameter of 7 mm) constituted by the elliptic ring-like members with the horizontal width of 7 mm×the vertical length of 12 mm extended below the ball chain. The outer diameter (Ra) of a small-diameter portion of the linear member was 3 mm, the length $L_A$ of the small-diameter portion was 50 mm, the outer diameter (Rb) of a large-diameter portion of the linear member was 7 mm, and the length of the large-diameter portion was 1350 mm.

Then, 131 g of granules (size of 5.8 mm) of a catalyst used to produce unsaturated aldehyde, the granules having a ring-like shape with an outer diameter of 5.0 mm, an inner diameter of 2.0 mm, and a height of 3.0 mm, were dropped and loaded into each of the two reaction tubes from above the reaction tube at a rate of the loaded volume of 30 cc per second. At the end of the dropping and the loading, the distance between a lower end of the linear member and an upper surface of a granule loaded layer was 197 mm. In other words, the length $L_x$ in FIG. 1 was 197 mm.

An atomic ratio among catalytic active elements of the catalyst used to produce the unsaturated aldehyde was as follows:

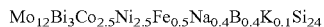
$$Mo_{12}Bi_3Co_{2.5}Ni_{2.5}Fe_{0.5}Na_{0.4}B_{0.4}K_{0.1}Si_{24}$$

As a result of dropping and loading the granules, clogging with the granules did not occur in both the two reaction tubes. The heights of the granule loaded layers in the two reaction tubes were 403 mm and 403 mm, namely the same. Because of the heights of the granule loaded layers being the same, it can be said that the loading densities in the two reaction tubes are also the same.

Example 7

Granules were loaded in accordance with the embodiment, illustrated in FIG. 2, using the funnel.

Two reaction tubes made of vinyl chloride and having an inner diameter of 25 mm and a tube length of 2000 mm (effective length of 2000 mm) were installed in the vertical direction. An aluminum-made funnel (of which leg portion had an opening diameter of 22.5 mm) was attached to a top of each of the two reaction tubes. A suspender was disposed inside a conical body portion of the aluminum-made funnel. One end of a linear member was fixed to the suspender such that the linear member extended downward in the vertical direction within the leg portion of the aluminum-made funnel and the reaction tube along a center axis of the reaction tube. The linear member was a linear member (length of 1580 mm) including a ball chain having an outer diameter of 3 mm and positioned on an upper side in the vertical direction, and a ring chain (outer diameter of 7 mm) constituted by elliptic ring-like members with a horizontal width of 7 mm×a vertical length of 12 mm and positioned on a lower side in the vertical direction, the ball chain and the ring chain being connected in series. Of the linear member extending downward in the vertical direction from the suspender, the ball chain with the outer diameter of 3 mm extended downward over a range of 20 mm from a lower end of the leg portion of the funnel, and the ring chain (outer diameter of 7 mm) constituted by the elliptic ring-like members with the horizontal width of 7 mm×the vertical length of 12 mm extended below the ball chain. The outer diameter (Ra) of a small-diameter portion of the linear member was 3 mm, the length $L_a$ of the small-diameter portion from the lower end of the leg portion of the funnel was 20 mm, the outer diameter (Rb) of a large-diameter portion of the linear member was 7 mm, and the length of the large-diameter portion was 1330 mm. The length $L_b$ through which the leg portion of the funnel was inserted in the reaction tube was 50 mm.

Then, 131 g of granules (size of 5.8 mm) of a catalyst used to produce unsaturated aldehyde, the granules being similar to those used in EXAMPLE 6 and having a ring-like shape with an outer diameter of 5.0 mm, an inner diameter of 2.0 mm, and a height of 3.0 mm, were dropped and loaded into each of the two reaction tubes from above the reaction tube through the funnel at a rate of the loaded volume of 30 cc per second. At the end of the dropping and the loading, the distance between a lower end of the linear member and an upper surface of a granule loaded layer was 197 mm. In other words, the length $L_x$ in FIG. 2 was 197 mm.

As a result of dropping and loading the granules, clogging with the granules did not occur in both the two reaction tubes. The heights of the granule loaded layers in the two reaction tubes were 403 mm and 403 mm, namely the same. Because of the heights of the granule loaded layers being the same, it can be said that the loading densities in the two reaction tubes are also the same.

Example 8

Granules were dropped and loaded at a rate of the loaded volume of 30 cc per second in a similar manner to that in EXAMPLE 6 except for using 265 g of granules (size of 5.8 mm) of a catalyst used to produce unsaturated carboxylic acid, the granules having a ring-like shape with an outer diameter of 5.0 mm, an inner diameter of 2.0 mm, and a height of 3.0 mm, instead of the granules (size of 5.8 mm) of the catalyst having been used to produce the unsaturated aldehyde, the latter granules having the ring-like shape with the outer diameter of 5.0 mm, the inner diameter of 2.0 mm, and the height of 3.0 mm. At the end of the dropping and the loading, the distance between the lower end of the linear member and an upper surface of a granule loaded layer was 185 mm. In other words, the length $L_x$ in FIG. 1 was 185 mm.

An atomic ratio among catalytic active elements of the catalyst used to produce the unsaturated carboxylic acid was as follows:

$$Mo_{12}V_{2.4}Nb_1Cu_{1.2}Ni_{8.5}Sb_{20}Si_2$$

As a result of dropping and loading the granules, clogging with the granules did not occur in both the two reaction tubes. The heights of the granule loaded layers in the two reaction tubes were 415 mm and 415 mm, namely the same. Because of the heights of the granule loaded layers being the same, it can be said that the loading densities in the two reaction tubes are also the same.

Example 9

Granules were dropped and loaded at a rate of the loaded volume of 30 cc per second in a similar manner to that in EXAMPLE 7 except for using 265 g of granules (size of 5.8 mm) of a catalyst used to produce unsaturated carboxylic acid, the granules being similar to those used in EXAMPLE 8 and having a ring-like shape with an outer diameter of 5.0 mm, an inner diameter of 2.0 mm, and a height of 3.0 mm, instead of the granules (size of 5.8 mm) of the catalyst having been used to produce the unsaturated aldehyde, the latter granules having the ring-like shape with the outer diameter of 5.0 mm, the inner diameter of 2.0 mm, and the height of 3.0 mm. At the end of the dropping and the loading, the distance between the lower end of the linear member and an upper surface of a granule loaded layer was 185 mm. In other words, the length $L_x$ in FIG. 2 was 185 mm.

As a result of dropping and loading the granules, clogging with the granules did not occur in both the two reaction tubes. The heights of the granule loaded layers in the two reaction tubes were 415 mm and 415 mm, namely the same. Because of the heights of the granule loaded layers being the same, it can be said that the loading densities in the two reaction tubes are also the same.

Comparative Example 1

Two reaction tubes made of vinyl chloride and having an inner diameter of 30 mm and a tube length of 1000 mm (effective length of 1000 mm) were installed in the vertical direction. An aluminum-made funnel (of which leg portion had an opening diameter of 22.5 mm) was attached to a top of each of the two reaction tubes. A suspender was disposed inside a conical body portion of the aluminum-made funnel. One end of a linear member was fixed to the suspender such that the linear member extended downward in the vertical direction within the leg portion of the aluminum-made funnel and the reaction tube along a center axis of the reaction tube. The linear member was a linear member (length of 420 mm) in the form of a ring chain (outer diameter of 7 mm) constituted by elliptic ring-like members with a horizontal width of 7 mm×a vertical length of 12 mm.

Then, 117 g of Raschig ring-shaped granules (size of 14.1 mm) made of silica-alumina and having an outer diameter of 10 mm, an inner diameter of 6 mm, and a height of 10 mm were dropped and loaded into each of the two reaction tubes from above the reaction tube through the funnel at a rate of the loaded volume of 30 cc per second. Clogging with the granules occurred in each of the two reaction tubes at an outlet of the funnel while the granules were being dropped and loaded, and the loading could not be performed completely to the end.

Comparative Example 2

Granules were dropped and loaded in a similar manner to that in EXAMPLE 1 except for using, as a linear member (length of 2400 mm), a nylon resin rope with an outer diameter of 3 mm.

As a result of dropping and loading the granules, clogging with the granules did not occur in both the two reaction tubes. However, the broken rates of the granules loaded in the two reaction tubes were significantly larger than those in EXAMPLE 1, namely 23% by weight and 22% by weight. The heights of the granule loaded layers in the two reaction tubes were different from each other, namely 390 mm and 385 mm.

Comparative Example 3

Two reaction tubes made of vinyl chloride and having an inner diameter of 25 mm and a tube length of 2000 mm (effective length of 2000 mm) were installed in the vertical direction. A suspender was disposed at a top of each of the two reaction tubes. One end of a linear member was fixed to the suspender such that the linear member extended downward in the vertical direction within the reaction tube along a center axis of the reaction tube. The linear member was a linear member (length of 1290 mm) in the form of a ring chain (outer diameter of 7 mm) constituted by elliptic ring-like members with a horizontal width of 7 mm×a vertical length of 12 mm.

Then, 287 g of granules (size of 5.4 mm) of a catalyst used to produce unsaturated carboxylic acid, the granules being similar to those used in EXAMPLE 4 and having a spherical shape with an average granule diameter of 5.4 mm, were dropped and loaded into each of the two reaction tubes from above the reaction tube through the funnel at a rate of the loaded volume of 30 cc per second. Clogging with the granules occurred in each of the two reaction tubes at an inlet of the reaction tube while the granules were being dropped and loaded, and the loading could not be performed completely to the end.

Comparative Example 4

Granules of a catalyst used to produce unsaturated aldehyde were loaded in a similar manner to that in EXAMPLE 3 except for using, as the linear member, a linear member (length of 1650 mm) including a ball chain having an outer diameter of 3 mm and positioned on an upper side in the vertical direction, and a ring chain (outer diameter of 7 mm) constituted by elliptic ring-like members with a horizontal width of 7 mm×a vertical length of 12 mm and positioned on a lower side in the vertical direction, the ball chain and the ring chain being connected in series. The outer diameter (Ra) of a small-diameter portion of the linear member was 3 mm, the length $L_a$ of the small-diameter portion from the lower end of the leg portion of the funnel was 20 mm, the outer diameter (Rb) of a large-diameter portion of the linear member was 7 mm, the length of the large-diameter portion was 1400 mm, and the length $L_b$ through which the leg portion of the funnel was inserted in the reaction tube was 50 mm.

Then, 273 g of granules (size of 5.2 mm) of the catalyst used to produce unsaturated aldehyde, the granules having the spherical shape with the average granule diameter of 5.2 mm, were dropped and loaded into each of the two reaction tubes from above the reaction tube through the funnel at a rate of the loaded volume of 30 cc per second.

As a result of dropping and loading the granules, clogging with the granules did not occur in both the two reaction tubes. The distances between lower ends of the linear members and upper surfaces of granule loaded layers were 25 mm and 35 mm. In other words, the lengths $L_x$ in FIG. 2 were 25 mm and 35 mm, namely less than 100 mm. The heights of the granule loaded layers in the two reaction tubes were different from each other, namely 505 mm and 495 mm.

According to the present invention, as will be understood from the above description, when loading the granules into the reaction tubes of the vertical multitube reactor, the granules can be smoothly loaded into the reaction tubes and the even granule loaded layers can be formed in the reaction tubes while damage of the granules is prevented without causing clogging of the reaction tubes with the granules.

While the present invention has been described in detail with reference to the specific embodiments, it is apparent to those skilled in the art that the present invention can be variously modified in practical use without departing from the purport and the scope of the present invention.

This application is based on Japanese Patent Application No. 2019-066219 filed on Mar. 29, 2019, the entire contents of which are incorporated herein by reference.

REFERENCE SIGNS LIST 1 reaction tube
2 linear member
2A small-diameter portion
2B large-diameter portion
3 granule loaded layer
4 suspender
5 funnel
10 granule

The invention claimed is:

1. A granule loading method, comprising:
loading granules into reaction tubes of a vertical multitube reactor, installed in a vertical direction, by dropping the granules from above each of the reaction tubes without using a funnel, the loading comprising inserting a linear member in the reaction tube, suspending the linear member in the reaction tube, and loading the granules through the linear member into the reaction tubes,
wherein the reaction tube has an effective length of 1000 mm or more,
wherein the linear member inserted in the reaction tube comprises a small-diameter portion positioned on an upper side and a large-diameter portion continuously extending from the small-diameter portion,
wherein the small-diameter portion has an outer diameter (Ra) in a range of from 0.2 to 5.0 mm,
wherein the large-diameter portion has an outer diameter (Rb) of 5.0 to 15.0 mm,
wherein the outer diameter (Rb) of the large-diameter portion is larger than the outer diameter (Ra) of the small-diameter portion,
wherein a length of the small-diameter portion from an upper end of the reaction tube is 0.10.0 mm or more, and
wherein a distance between an upper surface of a granule loaded layer formed inside the reaction tube and a lower end of the linear member inserted in the reaction tube is 100 mm or more.

2. A granule loading method, comprising:
loading granules into reaction tubes of a vertical multitube reactor, installed in a vertical direction, by dropping the granules from above each of the reaction tubes through a funnel comprising a funnel body portion positioned on a side receiving the granules and a leg portion having a cylindrical shape and positioned on a side discharging the granules, the loading comprising inserting the leg portion in the reaction tube, inserting a linear member through the leg portion of the funnel, and suspending the linear member in the reaction tube,
wherein the action tube has an effective length of 1000 mm or more,
wherein the linear member inserted in the reaction tube comprises a small-diameter portion positioned on an upper side and a large-diameter portion continuously extending from the small-diameter portion,
wherein the small-diameter portion has an outer diameter (Ra) in a range of from 0.2 to of 5.0 mm,
wherein the large-diameter portion has an outer diameter (Rb) in a range of from 5.0 to 15.0 mm,
wherein the outer diameter (Rb) of the large-diameter portion is larger than the outer diameter (Ra) of the small-diameter portion,
wherein a length of the small-diameter portion from a lower end of the leg portion of the funnel is 10.0 mm or more, and
wherein a distance between an upper surface of a granule loaded layer formed inside the reaction tube and a lower end of the linear member inserted in the reaction tube is 100 mm or more.

3. The method of claim 2, wherein an opening diameter of the leg portion of the funnel is not less than 0.6 times an inner diameter of the reaction tube.

4. The method of claim 1, wherein the reaction tube has an inner diameter in a range of from 22.0 to 35.0 mm.

5. The method of claim 1, wherein each of the granules has a size in a range of from 3.0 to 15.0 mm.

6. The method of claim 1, wherein the vertical multitube reactor is a reactor for producing unsaturated aldehyde.

7. The method of claim 1, wherein the vertical multitube reactor is a reactor for producing unsaturated carboxylic acid.

8. The method of claim 2, wherein the reaction tube has an inner diameter in a range of from 22.0 to 35.0 mm.

9. The method of claim 2, wherein an opening diameter of the leg portion of the funnel is not less than 0.6 times an inner diameter of the reaction tube, and
wherein the reaction tube has an inner diameter in a range of from 22.0 to 35.0 mm.

10. The method of claim 2, wherein each of the granules has a size in a range of from 3.0 to 15.0 mm.

11. The method of claim 2, wherein an opening diameter of the leg portion of the funnel is not less than 0.6 times an inner diameter of the reaction tube, and
wherein each of the granules has a size in a range of from 3.0 to 15.0 mm.

12. The method of claim 2, wherein the vertical multitube reactor is a reactor for producing unsaturated aldehyde.

13. The method of claim 2, wherein an opening diameter of the leg portion of the funnel is not less than 0.6 times an inner diameter of the reaction tube, and
wherein the vertical multitube reactor is a reactor for producing unsaturated aldehyde.

14. The method of claim 2, wherein the vertical multitube reactor is a reactor for producing unsaturated carboxylic acid.

15. The method of claim 2, wherein an opening diameter of the leg portion of the funnel is not less than 0.6 times an inner diameter of the reaction tube, and
wherein the vertical multitube reactor is a reactor for producing unsaturated carboxylic acid.

16. The method of claim 2, wherein the small-diameter portion has an outer diameter (Ra) in a range of from 1.0 to of 4.5 mm.

17. The method of claim 2, wherein the small-diameter portion has an outer diameter (Ra) in a range of from LO to of 4.5 mm.

18. The method of claim 1, wherein the large-diameter portion has an outer diameter (Rb) in a range of from 6.0 to 12.0 mm.

19. The method of claim 2, wherein the large-diameter portion has an outer diameter (Rb) in a range of from 6.0 to 12.0 mm.

20. The method of claim 1, wherein the small-diameter portion has an outer diameter (Ra) in a range of from 1.0 to of 4.5 mm, and
wherein the large-diameter portion has an outer diameter (Rb) in a range of from 6.0 to 12.0 mm.

* * * * *